United States Patent [19]

Schönafinger et al.

[11] Patent Number: 5,486,531
[45] Date of Patent: Jan. 23, 1996

[54] HYDROXYMETHYLFURAZANCARBOXYLIC ACID DERIVATIVES

[75] Inventors: Karl Schönafinger, Alzenau; Helmut Bohn, Schöneck, both of Germany

[73] Assignee: Cassella Aktiengesellschaft, Frankfurt am Main, Germany

[21] Appl. No.: 207,280

[22] Filed: Mar. 7, 1994

[30] Foreign Application Priority Data

Mar. 6, 1993 [DE] Germany .......... 43 07 105.8

[51] Int. Cl.⁶ .......... C07D 271/08; A61K 31/41
[52] U.S. Cl. .......... 514/364; 548/125; 546/271; 514/340
[58] Field of Search .......... 548/125; 546/271; 514/364, 340

[56] References Cited

U.S. PATENT DOCUMENTS 4,356,178 10/1982 Schonafinger et al. .......... 424/248
4,416,893 11/1983 Schonafinger et al. .......... 424/272

FOREIGN PATENT DOCUMENTS 0038438 10/1981 European Pat. Off. .

OTHER PUBLICATIONS

March, Advanced Organic Chemistry 3rd Ed. p. 351 (1985).

*Primary Examiner*—Robert Gerstl
*Attorney, Agent, or Firm*—Perman & Green

[57] ABSTRACT

The present invention relates to hydroxymethylfurazancarboxylic acid derivatives of the general formula I

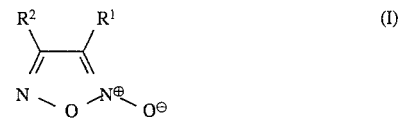

in which one of the radicals $R^1$ and $R^2$ represents hydroxymethyl and the other represents

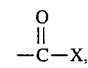

where X represents $NR^3R^4$, OH or $OR^7$, and $R^3$, $R^4$ and $R^7$ are defined as indicated in claim 1, to processes for their preparation and to their use.

10 Claims, No Drawings

HYDROXYMETHYLFURAZANCARBOXYLIC ACID DERIVATIVES

The present invention relates to hydroxymethylfurazancarboxylic acid derivatives, to processes for their preparation and to their use.

Different derivatives of 2-oxyfurazancarboxylic acid and 5-oxyfurazancarboxylic acid which carry a methyl group as the substituent on the furazan ring are already known, and are described, for example, in EP-B 38438 or EP-B 54873. However, derivatives of 2-oxyfurazancarboxylic acid and 5-oxyfurazancarboxylic acid which carry a hydroxymethyl group as the substituent have not previously been described.

The present invention relates to hydroxymethylfurazancarboxylic acid derivatives of the general formula I,

  (I)

in which one of the radicals $R^1$ and $R^2$ represents hydroxymethyl and the other represents

where X represents $NR^3R^4$ or OH or $OR^7$; $R^3$ and $R^4$, independently of each other, denote hydrogen, $(C_1-C_{20})$-alkyl, 1-phenyl-$(C_2-C_4)$-alkyl, 2-phenyl-$(C_3-C_4)$-alkyl, $(C_3-C_6)$-alkenyl, $(C_3-C_7)$-cycloalkyl, —$(CH_2)_n$—$NR^5R^6$, —$(CH_2)_n$—$OR^5$, —$(CH_2)_n$—$COOR^5$, —CH(Alk)—$COOR^5$, —$(CH_2)_n$—$CONR^5R^6$, —CH(Alk)—$CONR^5R^6$,

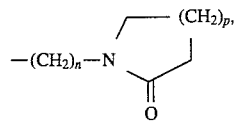

—$(CH_2)_n$—$NR^5$(COAlk), —$(CH_2)_n$—Ar or —$(CH_2)_n$—Het, or $R^3$ and $R^4$, together with the nitrogen atom linking them, form a heterocycle, which can also be substituted once or more than once by $(C_1-C_6)$-alkyl, $(C_3-C_7)$-cycloalkyl, $(C_1-C_4)$-alkoxy, amino, $(C_1-C_4)$-alklamino, di($(C_1-C_4)$-alkyl)amino, hydroxyl, acetoxy, benzyl, phenethyl or Ar;

$R^5$ and $R^6$, independently of each other, denote hydrogen, $(C_1-C_6)$-alkyl, $(C_3-C_6)$-alkenyl, $(C_3-C_7)$-cycloalkyl, benzyl, phenethyl or Ar;

$R^7$ denotes $(C_1-C_6)$-alkyl, $(C_3-C_7)$-cycloalkyl, benzyl or phenyl, or phenyl which is substituted once or more than once by $(C_1-C_4)$-alkyl, fluorine, chlorine or nitro;

Alk denotes $(C_1-C_6)$-alkyl;

Ar denotes an aryl radical having 6 to 12 C atoms which can also be substituted once or more than once by $(C_1-C_4)$-alkyl, $(C_1-C_4)$-alkoxy, amino, $(C_1-C_4)$-alkylamino, di($(C_1-C_4)$-alkyl)amino, $(C_1-C_6)$-alkanoylamino, sulphamoyl, fluorine, chlorine, bromine, hydroxyl, acetoxy, nitro, trifluoromethyl or cyano;

Het denotes a heterocyclic radical having 1 to 3 heteroatoms, which can also be substituted once or more than once by $(C_1-C_4)$-alkyl, $(C_1-C_4)$-alkoxy, amino, $(C_1-C_4)$-alklamino, di($(C_1-C_4)$-alkyl)amino, $(C_1-C_6)$-alkanoylamino, fluorine, chlorine, bromine, hydroxyl, acetoxy, nitro, cyano or Ar;

n represents 0, 1, 2, 3 or 4, m represents 1, 2, 3 or 4, p represents 1, 2 or 3; and pharmacologically acceptable salts thereof.

The present invention consequently embraces both compounds of the general formula Ia and compounds of the general formula Ib,

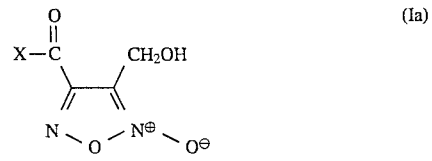  (Ia)

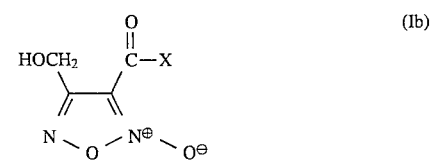  (Ib)

where X represents $NR^3R^4$, OH or $OR^7$, and $R^3$, $R^4$ and $R^7$ have the given meanings; it also embraces mixtures of the compounds of the general formulae Ia and Ib in arbitrary proportions.

Alkyl groups may be straight-chain or branched. This is also the case when they are substituted or are present, for example, in alkoxy groups or alkylamino groups, or as substituents on other radicals. Examples of the alkyl groups representing $R^3$, $R^4$, $R^5$, $R^6$, $R^7$ or Alk are methyl, ethyl, n-propyl, i-propyl, n-butyl, i-butyl, sec-butyl, tert-butyl, pentyl, hexyl or 1-methylpentyl, as are also octyl, decyl, dodecyl, hexadecyl, octadecyl or eicosyl of the alkyl groups representing $R^3$ or $R^4$.

The $(C_3-C_6)$-alkenyl groups representing $R^3$, $R^4$, $R^5$ or $R^6$ may also be straight-chain or branched. Examples are allyl, 2-butenyl, 3-butenyl, 2-methyl-2-butenyl, 3-methyl-2-butenyl, 2,3-dimethyl-2-butenyl, 2-hexenyl and 5-hexenyl.

A cyclopropyl, a cyclobutyl, a cyclopentyl, a cyclohexyl or a cycloheptyl radical are examples of the $(C_3-C_7)$-cycloalkyl radical representing $R^3$, $R^4$, $R^5$, $R^6$ or $R^7$, or being present as a substituent on the heterocycle formed from $R^3$ and $R^4$ and the nitrogen atom linking them. The cyclopentyl and the cyclohexyl radicals are preferred cycloalkyl radicals.

The aryl radical having 6 to 12 C atoms, and contained in the $(CH_2)_n$-Ar group, in $R^5$ and $R^6$, and as a substituent on the heterocyclic ring Het and on the heterocycle formed from $R^3$ and $R^4$ and the nitrogen atom linking them, can, for example, be an unsubstituted or substituted phenyl, 1-naphthyl, 2-naphthyl, 3-biphenylyl or 4-biphenylyl radical. Preferably, it is an unsubstituted or substituted phenyl radical.

—$(CH_2)_n$—Ar preferably represents phenyl, benzyl and phenethyl, which can be unsubstituted or substituted once or twice in the phenyl ring.

The heterocyclic radical having 1 to 3 heteroatoms, and contained in the —$(CH_2)_n$—Het group, can be aromatic and partially unsaturated and saturated, and can be fused. 5-rings, 6-rings and 7-rings are preferred ring sizes for the heterocycle. Preferred heteroatoms are nitrogen, oxygen and sulphur. Examples of heterocycles from which the radical Het is derived are azetidine, pyrrolidine, pyrrole, indole, pyrazole, imidazolidine, imidazoline, imidazole, 1,2,3-triazole, 1,2,4-triazole, tetrahydrofuran, furan, 1,3-dioxolane, tetrahydrothiophene, thiophene, benzothiophene, 1,3-dithiolane, 1,3-oxazoline, 1,3-oxazole, 1,3,4-oxadiazole, furazan, 1,3-thiazolidine, 1,3-thiazole, piperidine, 1,2,5,6-tetrahydropyridine, 1,4-dihydropyridine, pyridine, quinoline, isoquinoline, pyridazine, pyrimidine, piperazine, 1,2,3-triazine, 1,3,5-triazine, perhydropyran, 1,3-dioxane, 1,4-dioxane, 1,3-dithiane, dihydro-1,3-oxazine, morpholine, perhydro-1,4-thiazine and perhydroazepine. However, Het can also be a tetrazolyl radical, for example. Nitrogen heterocycles can be linked via a nitrogen atom or via a carbon atom. Preferred heterocyclic Het radicals are the 1-pyrrolyl radical, the 1- and the 2-imidazolyl radical, the 2-, 3- and the 4-pyridyl radical, and the 4-piperidinyl radical, and radicals of saturated heterocycles linked via a nitrogen atom, for example the pyrrolidino, the piperidino, the piperazino, the morpholino and the perhydro-1,4-thiazin-4-yl radicals.

The Ar aryl radicals and the Het heterocyclic radicals can also be substituted once or more than once. Examples of possible ($C_1$-$C_4$)-alkyl substituents are methyl, ethyl, n-propyl, i-propyl, i-butyl or tert-butyl;; of possible ($C_1$-$C_4$)-alkoxy substituents, methoxy, ethoxy, n-propoxy, i-propoxy, n-butoxy or i-butoxy; of possible ($C_1$-$C_4$)-alkylamino substituents, methylamino, ethylamino, i-propylamino, i-butylamino or tert-butylamino; of possible di(($C_1$-$C_4$)-alkyl)amino substituents, dimethylamino, diethylamino, diisopropylamino, methylethylamino or methyltert-butylamino; of ($C_1$-$C_6$)-alkanoylamino, formylamino, acetylamino, propionylamino, n-butyrylamino, i-butyrylamino, pivaloylamino or hexanoylamino. Examples of substituted derivatives of the phenyl radical which is preferred as the aryl radical are 2-, 3- or 4-methylphenyl, 4-tert-butylphenyl, 2-, 3- or 4-methoxyphenyl, 3-ethoxyphenyl, 2,3-, 3,4- or 3,5-dimethoxyphenyl, 3,4,5-trimethoxyphenyl, 3-aminophenyl, 3- or 4-dimethylaminophenyl, 4-acetylaminophenyl, 2-, 3- or 4-fluorophenyl, 2,3- or 3,4-difluorophenyl, 2-, 3- or 4-chlorophenyl, 2,3-, 3,4-, 3,5- or 2,6-dichlorophenyl, 4-bromophenyl, 4-hydroxyphenyl, 3-hydroxy-4-methoxyphenyl, 2-, 3- or 4-nitrophenyl, 4-chloro-3-nitrophenyl, 3- or 4-trifluoromethylphenyl, or 2-, 3- or 4-cyanophenyl. Examples of substituted heterocyclic Het radicals are 2,5-dimethyl-1-pyrrolyl, 2,5-dimethylpyrrolidino, 2,6-dimethylpiperidino, 4-methylpiperazino, 4-phenylpiperazino, 4-(2-methoxyphenyl)piperazino, 4-hydroxypiperidino, 4-aminopiperidino and 4-acetylpiperazino.

Examples of a heterocycle formed from $R^3$ and $R^4$ and the nitrogen atom linking them are pyrrolidine, piperidine, morpholine or piperazine, with, of the substituents which this latter heterocycle can carry, ($C_1$-$C_6$)-alkyl, ($C_3$-$C_7$)-cycloalkyl, benzyl, phenethyl and Ar preferably being located on the second nitrogen atom of the piperazine.

$R^7$ is preferably a straight-chain or branched ($C_1$-$C_4$)-alkyl radical, for example methyl, ethyl, n-propyl, i-propyl, n-butyl, i-butyl or t-butyl, in particular methyl.

The radical X can be chiral or achiral. Where the radical X is chiral, the compound can be present in racemic form or in the form of optical antipodes or diastereomers.

Preferably, X represents $NR^3R^4$ and one of the radicals $R^3$ and $R^4$ denotes hydrogen and the other has one of the given meanings, or the radicals $R^3$ and $R^4$, together with the nitrogen atom linking them, form a heterocycle, which can also be substituted once or more than once by ($C_1$-$C_6$)-alkyl, ($C_3$-$C_7$)-cycloalkyl, ($C_1$-$C_4$)-alkoxy, amino, ($C_1$-$C_4$)-alkylamino, di(($C_1$-$C_4$)-alkyl)amino, hydroxy, acetoxy, benzyl, phenethyl or Ar. Particularly preferably, one of the radicals $R^3$ and $R^4$ represents hydrogen and the other represents hydrogen, ($C_1$-$C_6$)-alkyl, —($CH_2$)$_n$$NR^5R^6$, where n represents 1, 2, 3 or 4 and $R^5$ and $R^6$ represent ($C_1$-$C_6$)-alkyl, —($CH_2$)$_n$$OR^5$, where n represents 2, 3 or 4 and $R^5$ represents hydrogen or ($C_1$-$C_4$)-alkyl, —($CH_2$)$_n$Ar, where n represents 0, 1, 2, 3 or 4 and Ar represents unsubstituted or mono- or polysubstituted phenyl, or —($CH_2$)$_n$Het, where n represents 1, 2, 3 or 4 and Het denotes a heterocyclic radical which, as the heteroatoms, contains 1 or 2 nitrogen atoms or 1 nitrogen atom and 1 oxygen atom, and can be substituted once or more than once by methyl groups, or the radicals $R^3$ and $R^4$, together with the nitrogen atom linking them, form a heterocycle which can also be subtituted once or more than once by methyl.

In addition to this, it is preferred if one of the radicals $R^3$ and $R^4$ represents hydrogen and the other denotes hydrogen, ($C_1$-$C_6$)-alkyl, —($CH_2$)$_n$$NR^5R^6$, where n represents 1, 2 or 3 and $R^5$ and $R^6$ represent ($C_1$-$C_6$)-alkyl, —($CH_2$)$_n$Ar, where n represents 1 or 2 and Ar represents an unsubstituted or monosubstituted or disubstituted phenyl radical, or —($CH_2$)$_n$Het, where n represents 1, 2 or 3 and Het represents a pyridiyl radical or an imidazolyl radical, or if the radicals $R^3$ and $R^4$, together with the nitrogen atom linking them, form a pyrrolidine ring or a piperazine ring which is substituted by methyl.

Preferred compounds of the general formula I are furthermore those in which

represents

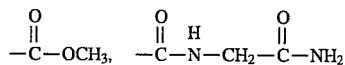

or, in particular

A particularly preferred compound of the general formula I is that in which $R^2$ represents hydroxymethyl and $R^1$ represents $CONH_2$, i.e. the 4-hydroxymethyl-2-oxyfurazan-3-carboxamide.

The compounds of the general formula I according to the invention, in which one of the radicals $R^1$ and $R^2$ represents —$CONR^3R^4$, can, for example, be prepared by the compound of the formula II, which is known from the literature (see Synthesis 1979, p. 977), being oxidized with an oxidizing agent to give the compound of the formula III or of the formula IV, or to give a mixture of the compounds of the formulae III and IV

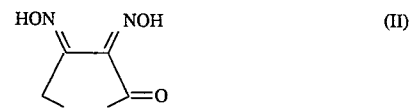

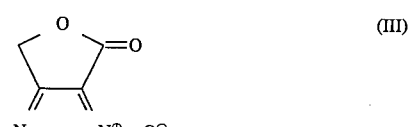

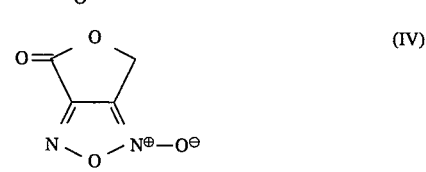

and the compounds of the formula III and/or IV subsequently being reacted with an amine $HNR^3R^4$, in which $R^3$ and $R^4$ are defined as indicated above. Conventional reagents, such as, for example, halogens, N-chlorosuccinimide and N-bromosuccinimide, alkali metal and alkaline earth metal hypochlorites, alkyl hypochlorites, such as, for example, tert-butyl hypochlorite, lead(IV) compounds, such as, for example, lead(IV)acetate, iron(III) salts, such as, for example, potassium ferricyanide, or nitrous gases, such as, for example, N₂O₃ or N₂O₄, can be employed as the oxidizing agents under these circumstances. Alkali metal and alkaline earth metal hypochlorites and alkyl hypochlorites are preferred oxidizing agents. The reaction is preferably carried out in a solvent, such as, for example, water, an alcohol, such as, for example, methanol or ethanol, an ether, an ester, such as, for example, ethyl acetate, a carboxylic acid, such as, for example, acetic acid, methylene chloride, chloroform, cyclohexane, benzene, toluene, chlorobenzene, dichlorobenzene, DMF or DMSO, or in a mixture of solvents, at temperatures of from −10° C. to 50° C., preferably of from −5° C. to 25° C. The compounds of the formulae III and/or IV can also be subjected directly to further reaction without being isolated.

The compounds of the formulae III and/or IV can also first be converted with alcohols $R^7OH$, where $R^7$ has the given meanings, into the esters of the general formulae Ic and/or Id according to the invention. The alcoholysis can also be carried out without isolating the compounds of the formulae III and/or IV; for example, the oxidation of the compound of the formula II can be carried out in such a way that the compounds of the general formulae Ic and/or Id are obtained directly.

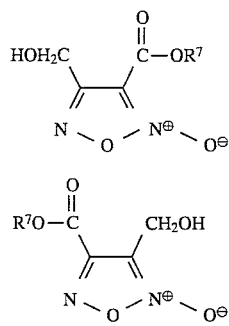

The esters of the general formulae Ic and/or Id according to the invention can in turn, where appropriate, be converted with amines $R^3R^4NH$ into amides according to the invention. This aminolysis, as well as that of the compounds of the formulae III and/or IV, can be carried out with or without a solvent. Examples of suitable solvents are water, alcohols, such as methanol, ethanol, n- or i-propanol, or n- or i-butanol, esters, such as ethyl acetate or isopropyl acetate, ethers, such as diethyl ether, dipropyl ether, dibutyl ether, tert-butyl methyl ether, tetrahydrofuran, dioxane, or ethylene glycol mono- or dialkyl ether or diethylene glycol mono- or dialkyl ether, hydrocarbons, such as toluene or xylene, chlorine hydrocarbons, such as dichloromethane, chlorobenzene or dichlorobenzene, or, for example, dimethylformamide, N-methylpyrrolidone or dimethyl sulphoxide. The reaction temperatures are between −10° and 140° C., preferably between 0° and 80° C.

The compounds of the general formula I, in which one of the radicals $R^1$ and $R^2$ represents $—CON^3R^4$, may also, furthermore, be obtained by initially reacting the compound of the formula II with amines $R^3R^4NH$, in which $R^3$ and $R^4$ are defined as indicated above, to give the compound of the general formula V

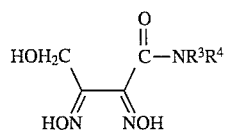

and then oxidizing the latter to give the compounds of the general formula I, it being possible in this case also to employ, at the relevant reaction step, the solvents and oxidizing agents which were listed, by way of example, in association with the previous process variants.

Where appropriate, the compounds of the general formula I according to the invention, which have been prepared by one of the abovementioned processes, can be converted, by modifying the substituents, into additional compounds of the general formula I according to the invention. For example, the side chain $—CO—NH—(CH_2)_nCOOR^5$ can be converted, by reaction with an amine $HNR^5R^6$, into the side chain $—CO—NH—(CH_2)_nCONR^5R^6$. An analogous conversion is possible with the side chain $—CO—NH—CH(Alk)—COOR^5$.

Compounds of the general formula I, in which one of the radicals $R^1$ and $R^2$ represents $—CON^3R^4$, can be obtained by reacting compounds of the general formula VI,

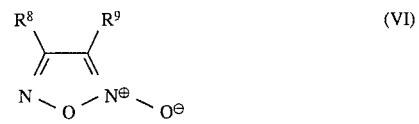

in which one of the radicals $R^8$ and $R^9$ represents hydroxymethyl and the other a reactive acid group, e.g.

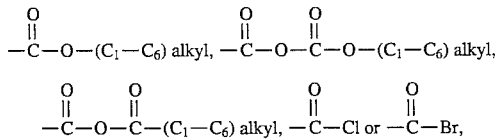

with an amine $HNR^3R^4$, in which $R^3$ and $R^4$ are defined as indicated above. Advantageously, the reaction is carried out in the presence of a base which neutralizes acids which arise. Preferred bases are alkali metal carbonates, such as sodium or potassium hydrogen carbonate or sodium or potassium carbonate; alkali metal hydroxides, such as sodium, potassium or lithium hydroxide; alkali metal alcoholates, such as sodium or potassium methylate, sodium or potassium ethylate or sodium tert-butylate; alkali metal hydrides, such as sodium or potassium hydride; alkali metal amides, such as sodium amide or lithium diisopropylamide; or organic bases, such as pyridine or triethylamine. These bases are preferably employed in molar quantities. Examples of suitable solvents, in each case depending on the nature of the reactive acid group, are water; alcohols, such as methanol, ethanol, n- or i-propanol, or n- or i-butanol; ethers, such as diethyl ether, dipropyl ether, dibutyl ether, tetrahydrofuran, dioxane, or ethylene glycol mono- or dialkyl ether or diethylene glycol mono- or dialkyl ether; hydrocarbons, such as toluene or xylene; chlorine hydrocarbons, such as dichloromethane, chlorobenzene or dichlorobenzene; or, for example, dimethylformamide, N-methylpyrrolidone or dimethyl sulphoxide. The reaction temperatures are between −10° C. and 80° C.

In the said reactions for preparing the compounds of the general formula I, these latter, or the intermediates of the general formulae III/IV, Ic/Id and VI, accrue, as a rule, in the form of isomeric mixtures; that is, in the case of the compounds of the general formula I, as a mixture of the compounds of the general formulae Ia and Ib. However, these latter can be resolved by known methods, such as by recrystallization or by chromatographic methods, in particular by column chromatography. The resolution can, therefore, be effected at the stage of an intermediate or at the stage of the compounds of the general formula I according to the invention. If the compounds to be resolved carry a basic or an acidic group, it can be advantageous firstly to convert them into a salt, and then resolve the mixture of the isomeric salts. Isomeric mixtures are also obtained when a pure isomer is itself, or dissolved in an inert solvent, heated at temperatures of 50° to 200° C. or photolysed at 0° to 50° C. By resolving the mixture obtained in this way it is thus possible to convert one isomer into the other.

Compounds of the general formula I, according to the invention, which contain a basic group can form acid addition salts with inorganic or organic acids. Examples of acids which are suitable for forming pharmacologically acceptable salts are: hydrogen chloride, hydrogen bromide, naphthalenedisulphonic acids, in particular naphthalenedisulphonic acid (1,5), and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acids. The acid addition salts can be prepared, as is customary, by combining the components, expediently in a suitable solvent or diluent. Correspondingly, acid addition salts which are prepared from the compounds of the general formula I for the purpose of isomer resolution can also, where appropriate, be converted directly, by anion exchange or via the free base, into pharmacologically acceptable acid addition salts which are desired for using the substances.

Compounds of the general formula I, according to the invention, which contain an acid group, for example a carboxylic acid group, can form salts with inorganic or organic bases. Examples of suitable, pharmacologically acceptable, salts are sodium salts, potassium salts, magnesium salts, calcium salts or ammonium salts, or salts with organic amines, for example ethanolamine or amino acids.

The hydroxymethylfurazancarboxylic acid derivatives of the general formula I, and their pharmacologically acceptable salts, possess valuable pharmacological properties which are based on the formation of nitrogen monoxide and on the effects of this compound. Thus, they lead to relaxation in smooth muscle and exhibit anti-adhesive and anti-aggregatory effects in the blood platelets. Nitrogen monoxide also plays a crucial role in learning processes, in the regulation of kidney functions, in immune defence and in erectile dysfunctions. The compounds of the general formula I can therefore be employed for the said indications, in particular for controlling and preventing disorders of the cardiovascular system, in particular for angina pectoris.

The pharmacological effect of the compounds of the formula I was determined in accordance with a modified method of Godfraind and Kaba (Arch. Int. Pharmacodyn. Ther. 196, (Suppl) 35 to 49, 1972) and of Schüman et al. (Naunyn-Schmiedeberg's Arch. Pharmacol. 289, 409 to 418, 1975). For this, spiral strips of the arteria pulmonalis of the guinea pig are depolarized, following equilibration in calcium-free Tyrode solution, with 40 mmol/l potassium. Addition of 0.5 mmol/l $CaCl_2$ then elicits a contraction. The relaxing effect of the test substance is determined by adding it cummulatively. The concentration of the test substance which inhibits the contraction by 50% ($=IC_{50}$, mol/l) is determined from the concentration-effect curve (abscissa: -log concentration (mol/l) of the test substance, ordinate: % inhibition of the maximum contraction, average value from 4 to 6 vessel strips).

$IC_{50}$ values obtained in this way for compounds according to the invention are given in the table below, as are the corresponding values for molsidomine and isosorbide 5-mononitrate, two active compounds which are frequently employed in treating angina pectoris. As compared with these latter substances, the compounds according to the invention are notable for exhibiting an effect which is clearly improved.

|  | $IC_{50}$(mol/l) |
| --- | --- |
| Compound 1 I (Example 1) | $8 \cdot 10^{-6}$ |
| Compound 3 I (Example 3) | $1.2 \cdot 10^{-5}$ |
| Compound of Example 4 I | $7.3 \cdot 10^{-6}$ |
| Compound of Example 8 | $8 \cdot 10^{-6}$ |
| Compound of Example 18 | $8 \cdot 10^{-6}$ |
| Compound of Example 23 | $1.5 \cdot 10^{-5}$ |
| Compound of Example 24 | $2 \cdot 10^{-6}$ |
| Compound of Example 26 | $1.1 \cdot 10^{-5}$ |
| Molsidomine | $3 \cdot 10^{-4}$ |
| Isosorbide 5-mononitrate | $>1 \cdot 10^{-4}$ |

The compounds of the general formula I, and their pharmacologically acceptable salts, can therefore be administered to humans as medicines on their own, in mixtures with each other, or in the form of pharmaceutical preparations which permit enteral or parenteral use and which contain, as the active constituent, an effective dose of at least one compound of the general formula I, or of a salt thereof, in addition to customary, pharmaceutically acceptable, carrier substances and additives.

The medicines can be administered orally, e.g. in the form of pills, tablets, lacquered tablets, coated tablets, hard and soft gelatin capsules, solutions, syrups, emulsions or suspensions, or aerosol mixtures. However, the administration can also be effected rectally, e.g. in the form of suppositories, or parenterally, e.g. in the form of injection or infusion solutions, or percutaneously, e.g. in the form of ointments or tinctures.

Pharmaceutically inert inorganic or organic carrier substances can be used for producing the pharmaceutical preparations. Lactose, corn starch or derivatives thereof, talc, or stearic acid or its salts, etc., can, for example, be used for producing pills, tablets, coated tablets and hard gelatin capsules. Examples of carrier substances for soft gelatin capsules and suppositories are fats, waxes, semi-solid and liquid polyols, natural or hardened oils, etc. Examples of suitable carrier substances for producing solutions and syrups are water, sucrose, invert sugar, glucose, polyols, etc. Examples of suitable carrier substances for producing injection solutions are water, alcohols, glycerol, polyols or vegetable oils.

In addition to the active compounds and carrier substances, the pharmaceutical preparations can also contain additives, such as, for example, fillers, extenders, disintegrants, binders, glidants, wetting agents, stabilizing agents, emulsifiers, preservatives, sweeteners, colourants, flavourants or aromatizing agents, or buffering substances, and, in addition, solvents or solubilizing agents, or agents for achieving a depot effect, as well as salts for altering the osmotic pressure, coating agents or antioxidants. They can also contain two or more compounds of the general formula I, or their pharmacologically acceptable salts, and other therapeutically active compounds as well.

Examples of other therapeutically active substances of this type are: β-receptor blockers, such as, for example, propranolol, pindolol or metoprolol; vasodilators, such as, for example, carbocromen; sedatives, such as, for example, barbituric acid derivatives, 1,4-benzodiazepine and meprobamate; diuretics, such as, for example, chlorothiazide; cardiac inotropic agents, such as, for example, digitalis preparations; antihypertensive agents, such as, for example, hydralazine, dihydralazine, ramipril, prazosin, clonidine and rauwolfia alkaloids; agents which lower the level of fatty acid in the blood, such as, for example bezafibrate and fenofibrate; agents for the prophylaxis of thromoboses, such as, for example, phenprocoumon.

The hydroxymethylfurazancarboxylic acid derivatives of the general formula I, their pharmacologically acceptable salts, and pharmaceutical preparations which contain the compounds of the general formula I, or their pharmacologically acceptable acid addition salts, as active compounds, can be used in humans in the control and prevention of disorders of the cardiovascular system, for example as antihypertensive medicines in the different forms of high blood pressure, in the control and prevention of angina pectoris, etc. In addition to this, they can also be employed for treating erectile dysfunctions. The dosage given can vary within wide limits and is to be matched to the individual circumstances in each individual case. In general, a daily dose of about 0.5 to 100 mg, preferably 1 to 20 mg, per human patient is appropriate in the case of oral administration. The daily dose is also of a similar order of magnitude, i.e. in general likewise 0.5 to 100 mg/patient, in the case of other forms of administration. The daily dose can be subdivided into a plurality of, e.g. 2 to 4, constituent doses.

EXAMPLES $^1$H-NMR spectra are measured in $D_6$-DMSO as the solvent. The chemical shifts, δ in ppm, the multiplicities (s=singlet, d=doublet, t=triplet and m=multiplet) and the proton number of the signals are given.

1. 4-Hydroxymethyl-N-isopropyl-2-oxyfurazan-3-carboxamide and 4-hydroxymethyl-N-isopropyl-5-oxyfurazan-3-carboxamide a) 4-Hydroxy-N-isopropyl-2,3-dioximinobutyramide 9.4 g of 3,4-dioximino-2-oxotetrahydrofuran are suspended in 50 ml of methanol, and 4.2 g of isopropylamine are added. The mixture is stirred for 3 h and then cooled in an ice bath. The solid material is filtered off with suction and recrystallized from methanol.

Yield: 8.5 g; m.p. 133°–134° C.

b) 4-Hydroxymethyl-N-isopropyl-2-oxyfurazan-3-carboxamide and 4-hydroxymethyl-N-isopropyl-5-oxyfurazan-3-carboxamide The mixture consisting of 10 g of the compound from step a), 120 ml of methylene chloride and 22 g of lead tetraacetate is stirred for 5 h. The water-soluble constituents are extracted three times by shaking with 100 ml of water on each occasion, and the organic phase is dried with sodium sulphate and concentrated in vacuo. The remaining oil is fractionated by column chromatography (silica gel, eluent: methylene chloride/methanol 99:1).

The compounds obtained are:

Compound 1 I: 2-Oxy derivative, yield 3.6 g (oil)
$^1$H-NMR: 1.20 (d, 6H), 4.08 (m, 1H), 4.69 (d, 2H), 5.77 (t, 1H), 8.25 (m, 1H)

Compound 1 II: 5-Oxy derivative, yield 1.8 g (oil)
$^1$H-NMR: 1.20 (d, 6H), 4.08 (m, 1H), 4.57 (d, 2H), 5.68 (t, 1H), 9.04 (m, 1H)

2. Methyl 4-hydroxymethyl-2-oxyfurazan-3-carboxylate and methyl 4-hydroxymethyl-5-oxyfurazan-3-carboxylate 8.9 g of lead tetraacetate are added, while cooling with ice, to a mixture consisting of 2.9 g of 3,4-dioximino-2-oxotetrahydrofuran, 30 ml of methylene chloride and 10 ml of methanol. After stirring at room temperature for two hours, 3 ml of triethylamine are added; the mixture is stirred for a further 30 min. and then diluted with 30 ml of methylene chloride and washed twice with 30 ml of water on each occasion. The organic phase is dried with sodium sulphate and concentrated in vacuo. The residue is stirred up with tert-butyl methyl ether, and the resulting solid is filtered off with suction. In order to resolve the isomers, recrystallization takes place from tert-butyl methyl ether.

Compound 2 I: 2-Oxy derivative: yield 1.9 g; m.p. 92°–94° C. $^1$H-NMR: 3.86 (s, 3H), 4.70 (s, 2H), 5.76 (m, 1H)

Compound 2 II: The 5-oxy derivative is contained in the recrystallization mother liquor.

3. 4-Hydroxymethyl-2-oxyfurazan-3-carboxamide and 4-hydroxymethyl-5-oxyfurazan-3-carboxamide a) 4-Hydroxymethyl-2-oxyfurazan-3-carboxamide (Compound 3I)

7.2 g of a concentrated aqueous solution of ammonia are added to 1.9 g of methyl 4-hydroxymethyl-2-oxyfurazan-3-carboxylate from Example 2) in 25 ml of methanol. After 1 h, the mixture is concentrated in vacuo and the residue is recrystallized from water.

Yield: 1.1 g; m.p. 128°–130° C. $^1$H-NMR: 4.72 (d, 2H), 5.73 (t, 1H), 7.85 (m, 1H), 8.41 (m, 1H)

The structure was confirmed by X-ray structural analysis.

b) 4-Hydroxymethyl-5-oxyfurazan-3-carboxamide (Compound 3II)

In accordance with a), the methyl 4-hydroxymethyl-5-oxyfurazan-3-carboxylate from Example 2), which is contained in the recrystallization mother liquor, is reacted with ammonia. The product is purified by column chromatography (silica gel, eluent methylene chloride/methanol 98:2). M.p. 145°–147° C. $^1$H-NMR: 4.57 (d, 2H), 5.60 (t, 1H), 8.20 (m, 1H), 8.50 (m, 1H)

The following are obtained in an analogous manner:

4 I. 4-Hydroxymethyl-N-methyl-2-oxyfurazan-3-carboxamide

M.p. 104°–106° C. $^1$H-NMR: 2.80 (s, 3H), 4.72 (s, 2H), 5.70 (m, 1H), 8.41 (m, 1H)

4 II. 4-Hydroxymethyl-N-methyl-5-oxyfurazan-3-carboxamide

M.p. 86°–88° C. $^1$H-NMR: 2.91 (d, 3H), 4.57 (d, 2H), 5.63 (t, 1H), 9.12 (m, 1H)

5. 4-Hydroxymethyl-2-oxyfurazan-3-carboxylic acid (4-methylpiperazide) hydrochloride M.p. 210° C. (decomp.) $^1$H-NMR: 2.82 (s, 3H), 3.0–4.4 (m, 8H), 4.62 (s, 2H), 9.0–10.0 (m, 2H)

6. N-(2-Diisopropylaminoethyl)-4-hydroxymethyl-2-oxyfurazan-3-carboxamide hydrochloride M.p. 189°–191° C. $^1$H-NMR: 1.40 (d, 12H), 3.2 (m, 2H), 3.70 (m, 4H), 4.74 (s, 2H), 5.75 (m, 1H), 8.84 (m, 1H), 10.30 (m, 1H)

7. N-Butyl-4-hydroxymethyl-2-oxyfurazan-3-carboxamide

Oil $^1$H-NMR: 0.91 (t, 3H), 1.30 (m, 2H), 1.45 (m, 2H), 3.26 (m, 2H), 4.72 (s, 2H), 5.75 (m, 1H), 8.45 (m, 1H)

8. 4-Hydroxymethyl-N-(3-pyridylmethyl)-2-oxyfurazan-3-carboxamide hydrochloride

M.p. 185° C. (decomp.) $^1$H-NMR: 4.68 (d, 2H), 4.72 (s, 2H), 8.0 (m, 1H), 8.51 (m, 1H), 8.80 (m, 1H), 8.90 (s, 1H), 9.30 (m, 1H)

9. N-Benzyl-4-hydroxymethyl-2-oxyfurazan-3-carboxamide

M.p. 94°–96° C. $^1$H-NMR: 4.48 (s, 2H), 4.73 (s, 2H), 5.80 (m, 1H), 7.30 (m, 5H), 8.85 (m, 1H)

10. N-Carbamoylmethyl-4-hydroxymethyl-2-oxyfurazan-3-carboxamide

M.p. 186°–188° C. $^1$H-NMR: 3.85 (d, 2H), 4.74 (t, 2H), 5.73 (t, 1H), 7.20 (m, 1H), 7.50 (m, 1H), 8.60 (m, 1H)

11. 4-Hydroxymethyl-2-oxyfurazan-3-carboxylic acid pyrrolidide

Oil $^1$H-NMR: 1.85 (m, 4H), 3.47 (m, 4H), 4.60 (d, 2H), 5.78 (t, 1H)

12. 4-Hydroxymethyl-N-isobutyl-2-oxyfurazan-3-carboxamide

Oil $^1$H-NMR: 0.89 (d, 6H), 1.84 (m, 1H), 3.12 (m, 2H), 4.72 (d, 2H), 5.77 (t, 1H)

13. 4-Hydroxymethyl-N-(2-hydroxyethyl)-2-oxyfurazan-3-carboxamide

M.p. 69°–71° C. $^1$H-NMR: 3.36 (m, 2H); 3.53 (m, 2H); 4.72 (d, 2H); 4.86 (t, 1H); 5.72 (t, 1H); 8.40 (m, 1H)

14. 4-Hydroxymethyl-N-(2-diisopropylaminoethyl)-5-oxyfurazan-3-carboxamide hydrochloride M.p. 167°–170° C. $^1$H-NMR: 1.35 (q, 12H); 3.20 (m, 2H); 3.69 (m, 4H); 4.57 (s, 2H); 5.69 (m, 1H); 9.48 (m, 1H); 10.23 (m, 1H)

15. 4-Hydroxymethyl-N-(3-(imidazol-1-yl)-propyl)-5-oxyfurazan-3-carboxamide

M.p. 145°–147° C. $^1$H-NMR: 1.95 (m, 2H); 3.25 (m, 2H), 4.00 (m, 2H); 4.54 (s, 2H); 5.71 (m, 1H); 6.87 (s, 1H); 7.18 (s, 1H); 7.62 (s, 1H); 9.27 (m, 1H)

16. 4-Hydroxymethyl-N-(2-hydroxyethyl)-5-oxyfurazan-3-carboxamide

M.p. Oil $^1$H-NMR: 3.32 (m, 2H); 3.52 (m, 2H); 4.55 (d, 2H); 4.70 (m, 1H); 5.67 (t, 1H); 9.09 (m, 1H)

17. 4-Hydroxymethyl-N,N-dimethyl-2-oxyfurazan-3-carboxamide

M.p. Oil $^1$H-NMR: 2.98 (d, 6H); 4.58 (d, 2H); 5.84 (t, 1H)

18. 4-Hydroxymethyl-N-(2-methoxyethyl)-2-oxyfurazan-3-carboxamide

M.p. Oil $^1$H-NMR: 3.26 (s, 3H); 3.47 (s, 4H); 4.73 (s, 2H); 5.77 (m, 1H); 8.48 (m, 1H)

19. Isopropyl 4-hydroxymethyl-2-oxyfurazan-3-carboxylate

Oil $^1$H-NMR: 1.30 (d, 6H); 4.69 (d, 2H); 5.17 (m, 1H); 5.70 (t, 1H)

20. 4-Hydroxymethyl-N-(3-(imidazol-1-yl)-propyl)-2-oxyfurazan-3-carboxamide

M.p. 122°–125° C. $^1$H-NMR: 1.93 (m, 2H); 3.23 (m, 2H); 4.00 (m, 2H); 4.72 (s, 2H); 5.89 (m, 1H); 6.90 (s, 1H); 7.18 (s, 1H); 7.63 (s, 1H); 8.60 (m, 1H)

21. 4-Hydroxymethyl-N-(3-hydroxypropyl)-5-oxyfurazan-3-carboxamide

Oil $^1$H-NMR: 1.69 (m, 2H); 3.33 (m, 2H); 3.47 (m, 2H); 4.52 (m, 3H); 5.65 (t, 1H); 9.10 (m, 1H)

22. 4-Hydroxymethyl-N-(3-pyridylmethyl)-5-oxyfurazan-3-carboxamide

M.p. 154°–156° C. $^1$H-NMR: 4.51 (d, 2H); 4.59 (d, 2H); 5.63 (t, 1H); 7.39 (m, 1H); 7.75 (m, 1H); 8.49 (m, 1H); 8.59 (s, 1H); 9.78 (m, 1H)

23. 4-Hydroxymethyl-N-((S)-1-phenylethyl)-2-oxyfurazan-3-carboxamide

M.p. Oil $\alpha_D^{20}$=+17.5 (c=5.472, MeOH) $^1$H-NMR:: 1.48 (d, 3H); 4.69 (d, 2H); 5.10 (m, 1H); 5.87 (t, 1H); 7.33 (m, 5H); 8.84 (d, 1H)

24. 4-Hydroxymethyl-N-((R)-1-phenylethyl)-2-oxyfurazan-3-carboxamide

Oil $\alpha_D^{20}$=−16.7 (c=5.618, MeOH) $^1$H-NMR: 1.48 (d, 3H); 4.69 (d, 2H); 5.10 (m, 1H); 5.87 (t, 1H); 7.33 (m, 5H); 8.84 (d, 1H)

25. 4-Hydroxymethyl-N-octadecyl-2-oxyfurazan-3-carboxamide

M.p. 75°–77° C. $^1$H-NMR: 0.6–1.6 (m, 35H); 3.30 (m, 2H); 4.70 (m, 2H); 5.76 (m, 1H); 8.50 (m, 1H)

26. 4-Hydroxymethyl-N-[2-(4-sulphamoylphenyl)-ethyl]-2-oxyfurazan-3-carboxamide

M.p. 152°–154° C. $^1$H-NMR: 2.90 (m, 2H); 3.53 (m, 2H); 4.72 (s, 2H); 5.80 (m, 1H); 7.23 (m, 2H); 7.42 (d, 2H); 7.77 (d, 2H); 8.57 (m, 1H)

27. Methyl 4-hydroxymethyl-2-oxyfurazan-3-carboxylate a) 3,4-Dioximino-2-oxotetrahydrofuran A solution of 30.4 g of sodium nitrite in 60 ml of water is added dropwise, while cooling with ice, to a mixture consisting of 49 g of tetronic acid, 43.4 g of concentrated hydrochloric acid and 100 ml of water. The mixture is subsequently stirred for 30 min. and a solution of 30.6 g of hydroxylamine hydrochloride in 60 ml of water is then added. This mixture is subsequently stirred for a further 3 hours while cooling with ice, and the product is then filtered off with suction, washed with water and sucked dry.

Yield: 76.3 g (moist) M.P. 160°–180° C. (decomp.)

3,4-Dioximino-2-oxotetrahydrofuran is also obtained in 60% yield from ethyl 4-tert-butoxyacetoacetate by treating with aqueous sulphuric acid or hydrochloric acid, treating the tetronic acid which is formed as an intermediate with nitrous acid, and reacting with hydroxylamine hydrochloride.

b) Methyl 4-hydroxymethyl-2-oxyfurazan-3-carboxylate

A solution of 18.9 g of tert-butyl hypochlorite in 25 ml of ethyl acetate is added rapidly dropwise to a mixture, which is cooled in an ice bath, consisting of 27 g of 3,4-dioximino-2-oxotetrahydrofuran and methanol (210 ml). Potassium acetate (18.5 g) is subsequently added in small portions, while cooling, and the mixture is then stirred overnight in the ice bath which gradually warms to room temperature. The mixture is concentrated in vacuo, the residue is taken up in water, and the product is extracted with ethyl acetate. After drying and concentrating the ethyl acetate phase, recrystallization takes place from isopropyl acetate.

Yield: 14.7 g M.p. 97°–98° C.

Methyl 4-hydroxymethyl-2-oxyfurazan-3-carboxylate is also obtained by the same process when solid 70 per cent calcium hypochlorite is used instead of the solution of tert-butyl hypochlorite in ethyl acetate.

28. 4-Hydroxymethyl-N-cyclohexyl-2-oxyfurazan-3-carboxamide

M.p. 97°–98° C. $^1$H-NMR: 1.10–1.85 (m, 10H); 3.74 (m, 1H); 4.72 (s, 2H); 5.82 (m, 1H); 8.25 (m, 1H)

29. 4-Hydroxymethyl-N-ethoxycarbonylmethyl-2-oxyfurazan-3-carboxamide

M.p. Oil $^1$H-NMR: 1.23 (t, 3H); 4.08 (d, 2H); 4.15 (q, 2H); 4.74 (d, 2H); 5.73 (t, 1H); 8.81 (m, 1H)

30. 4-Hydroxymethyl-N-(2-acetylaminoethyl)-2-oxyfurazan-3-carboxamide

M.p. 126°–128° C. $^1$H-NMR: 1.79 (s, 1H), 3.20 (m, 2H); 3.33 (m, 2H); 4.75 (s, 2H); 5.76 (m, 1H); 7.80 (m, 1H); 8.51 (m, 1H)

31. 4-Hydroxymethyl-N-allyl-2-oxyfurazan-3-carboxamide

M.p. Oil $^1$H-NMR:: 3.90 (s, 2H); 4.76 (s, 2H); 5.17 (m, 2H); 5.83 (m, 1H); 5.78 (m, 1H); 8.67 (m, 1H)

32. 4-Hydroxymethyl-N-(1-ethoxycarbonylethyl)-2-oxyfurazan-3-carboxamide

M.p. Oil $^1$H-NMR: 1.32 (t, 3H); 1.40 (d, 3H); 4.32 (q, 2H); 4.50 (m, 1H); 4.73 (d, 2H); 5.71 (t, 1H); 8.81 (m, 1H)

33. 4-Hydroxymethyl-N-[3-(2-oxopyrrolidin-1-yl)-propyl]-2-oxyfurazan-3-carboxamide M.p. 120°–122° C. $^1$H-NMR: 1.65 (m, 2H); 1.92 (m, 2H); 2.22 (m, 2H); 3.21 (m, 4H); 3.38 (m, 2H); 4.74 (s, 2H); 5.73 (m, 1H); 8.55 (m, 1H)

34. 4-Hydroxymethyl-N-[2-(3,4-dimethoxyphenyl)ethyl]-2-oxyfurazan-3-carboxamide

M.p. 128°–130° C. $^1$H-NMR: 2.77 (t, 2H); 3.46 (t, 2H); 3.73 (s, 3H); 3.74 (s, 3H); 4.70 (s, 2H); 5.72 (m, 1H); 6.70–6.91 (m, 3H); 8.44 (m, 1H)

Pharmaceutical preparations are described in the following Examples A to F.

Example A

Soft gelatin capsules, containing 5 mg of active compound per capsule:

|  | per capsule |
| --- | --- |
| Active compound | 5 mg |
| Triglyceride mixture fractionated from coconut oil | 150 mg |
| Capsule content | 155 mg |

Example B

Injection solution, containing 1 mg of active compound per ml:

|  | per ml |
| --- | --- |
| Active compound | 1.0 mg |
| Polyethylene glycol 400 | 0.3 ml |
| Sodium chloride | 2.7 mg |
| Water for injection purposes ad | 1 ml |

Example C

Emulsion, containing 3 mg of active compound per 5 ml

|  | per 100 ml of emulsion |
| --- | --- |
| Active compound | 0.06 g |
| Neutral oil | q.s. |
| Sodium carboxymethyl cellulose | 0.6 g |
| Polyoxyethylene stearate | q.s. |
| Glycerol, pure | 0.2 to 2.0 g |
| Flavourant | q.s. |
| Water (desalted or distilled) ad | 100 ml |

Example D

Rectal form of drug, containing 4 mg of active compound per suppository

|  | per suppository |
| --- | --- |
| Active compound | 4 mg |
| Suppository matrix ad | 2 mg |

Example E

Tablets, containing 2 mg of active compound per tablet

|  | per tablet |
| --- | --- |
| Active compound | 2 mg |
| Lactate (finely ground) | 2 mg |
| Corn starch (white) | 150 mg |
| Lactose | 60 mg |
| Microcrystalline cellulose | 50 mg |
| Polyvinylpyrrolidone | 20 mg |

|  | per tablet |
| --- | --- |
| Magnesium stearate | 2 mg |
| Sodium carboxymethyl starch | 25 mg |
|  | 311 mg |

Example F

Coated tablets, containing 1 mg of active compound per coated tablet

|  | per coated tablet |
| --- | --- |
| Active compound | 1 mg |
| Corn starch | 100 mg |
| Lactose | 60 mg |
| Calcium hydrogen phosphate | 30 mg |
| Soluble starch | 3 mg |
| Magnesium stearate | 2 mg |
| Colloidal silicic acid | 4 mg |
|  | 200 mg |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Hydroxymethylfurazancarboxylic acid derivatives of the formula I

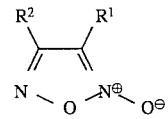

in which one of the radicals $R^1$ and $R^2$ represents hydroxymethyl and the other represents

where

X represents $NR^3R^4$ or OH or $OR^7$;

$R^3$ and $R^4$, independently of each other, denote hydrogen, $(C_1-C_{20})$-alkyl, 1-phenyl-$(C_2-C_4)$-alkyl, 2-phenyl-$(C_3-C_4)$-alkyl, $(C_3-C_6)$-alkenyl, $(C_3-C_7)$-cycloalkyl, $-(CH_2)_n-NR^5R^6$, $-(CH_2)_n-OR^5$, $-(CH_2)_m-COOR^5$, $-CH(Alk)-COOR^5$ $-(CH_2)_m-CONR^5R^6$, $-CH(Alk)-CONR^5R^6$,

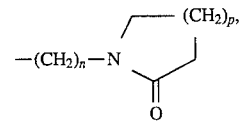

$-(CH_2)_n-NR^5(COAlk)$, $-(CH_2)_n-Ar$ or $-(CH_2)_n-Het$, or $R^3$ and $R^4$, together with the nitrogen atom linking them, form a heterocycle, which can also be substituted once or more than once by $(C_1-C_6)$-alkyl, $(C_3-C_7)$-cycloalkyl, $(C_1-C_4)$-alkoxy, amino, $(C_1-C_4)$-alkylamino, di($(C_1-C_4)$-alkyl)amino, hydroxyl, acetoxy, benzyl, phenethyl or Ar;

R⁵ and R⁶, independently of each other, denote hydrogen, $(C_1-C_6)$-alkyl, $(C_3-C_6)$-alkenyl, $(C_3-C_7)$-cycloalkyl, benzyl, phenethyl or Ar;

R⁷ denotes $(C_1-C_6)$-alkyl, $(C_3-C_7)$-cycloalkyl, benzyl or phenyl, or phenyl which is substituted once or more than once by $(C_1-C_4)$-alkyl, fluorine, chlorine or nitro;

Alk denotes $(C_1-C_6)$-alkyl;

Ar denotes an aryl radical having 6 to 12 C atoms which can also be substituted once or more than once by $(C_1-C_4)$-alkyl, $(C_1-C_4)$-alkoxy, amino, $(C_1-C_4)$-alkylamino, di$((C_1-C_4)$-alkyl)amino, $(C_1-C_6)$-alkanoylamino, sulphamoyl, fluorine, chlorine, bromine, hydroxyl, acetoxy, nitro, trifluoromethyl or cyano;

Het denotes a heterocyclic radical having 1 to 3 heteroatoms, which can also be substituted once or more than once by $(C_1-C_4)$-alkyl, $(C_1-C_4)$-alkoxy, amino, $(C_1-C_4)$-alkylamino, di$((C_1-C_4)$-alkyl)amino, $(C_1-C_6)$-alkanoylamino, fluorine, chlorine, bromine, hydroxyl, acetoxy, nitro, cyano or Ar;

n represents 0, 1, 2, 3 or 4, m represents 1, 2, 3 or 4, p represents 1, 2 or 3; and pharmacologically acceptable salts thereof.

2. Hydroxymethylfurazancarboxylic acid derivatives of the formula I according to claim 1, characterized in that X represents NR³R⁴, and in that one of the radicals R³ and R⁴ represents hydrogen and the other radical possesses one of the definitions given in claim 1, or in that R³ and R⁴, together with the nitrogen atom linking them, form a heterocycle, which can also be substituted once or more than once by $(C_1-C_6)$-alkyl, $(C_3-C_7)$-cycloalkyl, $(C_1-C_4)$-alkoxy, amino, $(C_1-C_4)$-alkylamino, di$((C_1-C_4)$-alkyl)amino, hydroxyl, acetoxy, benzyl, phenethyl or Ar.

3. Hydroxymethylfurazancarboxylic acid derivatives of the formula I according to claim 1, characterized in that X represents NR³R⁴, and in that one of the radicals R³ and R⁴ represents hydrogen and the other represents hydrogen, $(D_1-C_6)$-alkyl, or —$(CH_2)_n$NR⁵R⁶, where n denotes 1, 2, 3 or 4 and R⁵ and R⁶ denotes $(C_1-C_6)$-alkyl, or —$(CH_2)_n$OR⁵, where n denotes 2, 3 or 4 and R⁵ denotes hydrogen or $(C_1-C_4)$-alkyl, or —$(CH_2)_n$Ar, where n denotes 0, 1, 2, 3 or 4 and Ar denotes unsubstituted or mono- or polysubstituted phenyl, or —$(CH_2)_n$Het, where n denotes 1, 2, 3 or 4 and Het denotes a heterocyclic ring, which contains, as heteroatoms, 1 or 2 nitrogen atoms or 1 nitrogen atom and 1 oxygen atom, and which can be substituted once or more than once by methyl groups, or in that R³ and R⁴, together with the nitrogen atoms linking them, form a heterocycle which can also be substituted once or more than once by methyl groups.

4. Hydroxymethylfurazancarboxylic acid derivatives of the formula I according to claim 1, characterized in that X represents NR³R⁴, and in that one of the radicals R³ and R⁴ represents hydrogen and the other represents hydrogen, $(C_1-C_6)$-alkyl, or —$(CH_2)_n$NR⁵R⁶, where n denotes 1, 2 or 3 and R⁵ and R⁶ denote $(C_1-C_6)$-alkyl, —$(CH_2)_n$Ar, where n denotes 1 or 2 and Ar denotes unsubstituted or mono- or disubstituted phenyl, or —$(CH_2)_n$Het, where n denotes 1, 2 or 3 and Het denotes pyridyl or imidazolyl, or in that the radicals R³ and R⁴, together with the nitrogen atom linking them, form a pyrrolidine ring or a piperazine ring which is substituted by methyl.

5. Hydroxymethylfurazancarboxylic acid derivatives of the formula I according to claim 1, characterized in that one of the radicals R¹ and R² represents hydroxymethyl and the other represents

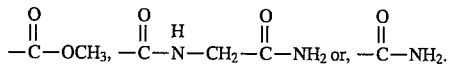

6. Hydroxymethylfurazancarboxylic acid derivatives of the formula I according to claim 1, characterized in that R¹ represents hydroxymethyl.

7. Hydroxymethylfurazancarboxylic acid derivatives of the formula I according to claim 1, characterized in that R² represents hydroxymethy.

8. 4-Hydroxymethyl-2-oxyfurazan-3-carboxamide.

9. Process for the treatment of angina pectoris high blood pressure and erectile dysfunctions, which comprises administering effective amounts of a hydroxymethylfurazancarboxylic acid derivative of formula I according to claim 1, or a pharmacologically acceptable acid addition compound thereof, to a patient in need thereof.

10. Pharmaceutical composition for the treatment of angina pectoris high blood pressure and erectile dysfunctions, characterized in that it contains one or more hydroxymethylfurazancarboxylic acid derivatives of formula I as claimed in claim 1, or a pharmacologically acceptable acid addition salt thereof as active compound, together with pharmaceutically acceptable excipients and additives.

* * * * *